US011002866B2

(12) United States Patent
Yamakawa (10) Patent No.: US 11,002,866 B2
(45) Date of Patent: May 11, 2021

(54) SCATTERING ESTIMATION METHOD AND IMAGE PROCESSOR (71) Applicant: Shimadzu Corporation, Kyoto (JP)

(72) Inventor: Yoshiyuki Yamakawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/627,151

(22) PCT Filed: Jul. 25, 2017

(86) PCT No.: PCT/JP2017/026917
§ 371 (c)(1),
(2) Date: Dec. 27, 2019

(87) PCT Pub. No.: WO2019/021376
PCT Pub. Date: Jan. 31, 2019

(65) Prior Publication Data
US 2020/0174144 A1 Jun. 4, 2020

(51) Int. Cl.
G01T 1/29 (2006.01)
G06T 11/00 (2006.01)
A61B 6/00 (2006.01)

(52) U.S. Cl.
CPC .......... *G01T 1/2985* (2013.01); *A61B 6/5258* (2013.01); *G06T 11/005* (2013.01)

(58) Field of Classification Search
CPC .... G06T 11/005; G01T 1/2985; A61B 6/5258
See application file for complete search history.

(56) References Cited

U.S. PATENT DOCUMENTS

| 8,575,554 B2 | 11/2013 | Qian et al. | |
|---|---|---|---|
| 2013/0026370 A1* | 1/2013 | Qian | G06T 11/005 250/362 |
| 2018/0325485 A1* | 11/2018 | Maslowski | G06T 5/00 |

OTHER PUBLICATIONS

Written Opinion of the International Searching Authority for PCT application No. PCT/JP2017/026917, submitted with a machine translation (partial).
Andrew S. Goggin et al., "A Model for Multiple Scatters in Fully 3D PET," Nuclear Science Symposium and Medical Imaging Conference, 1994, vol. 4, pp. 1609-1613.

* cited by examiner

*Primary Examiner* — Michael C Bryant
(74) *Attorney, Agent, or Firm* — Muir Patent Law, PLLC (57) ABSTRACT A scattering estimation method includes determining a convolution kernel for smoothing a single scattering distribution based on a scattered radiation index value (R) of a radioactive image (5) (S4) and fitting, to positron emission tomography measurement data, a scattering distribution smoothed by applying the convolution kernel to the single scattering distribution (S5).

7 Claims, 9 Drawing Sheets

(A) GENERATE RADIOACTIVE IMAGE (B) RECONSTRUCT RADIOACTIVE IMAGES WITH VARIED PARAMETERS (C) CHANGES OF SCATTER FRACTIONS OF RECONSTRUCTED IMAGES

FIG. 7

(D) DIFFERENCE VALUES BETWEEN SCATTER FRACTIONS OF RECONSTRUCTED IMAGES

(E) FIT SCATTERING DISTRIBUTION TO POSITRON EMISSION TOMOGRAPHY DATA

FIG. 8

(A) IMAGES WITH VARIED PARAMETERS (ABDOMEN)

(B) CHANGES OF SCATTER FRACTIONS OCCURRING WHEN PARAMETER IS VARIED (ABDOMEN)

(C) DIFFERENCE VALUES BETWEEN SCATTER FRACTIONS OCCURRING WHEN PARAMETER IS VARIED (ABDOMEN)

FIG. 9

(A) IMAGES WITH VARIED PARAMETERS (PELVIS)

(B) CHANGES OF SCATTER FRACTIONS OCCURRING WHEN PARAMETER IS VARIED (PELVIS)

(C) DIFFERENCE VALUES BETWEEN SCATTER FRACTIONS OCCURRING WHEN PARAMETER IS VARIED (PELVIS)

FIG. 10

FIRST MODIFIED EXAMPLE

FIG. 11

SCATTERING ESTIMATION METHOD AND IMAGE PROCESSOR

TECHNICAL FIELD

The present invention relates to a scattering estimation method and an image processor, and more particularly, it relates to a scattering estimation method for measurement data of a positron emission tomography apparatus and an image processor.

BACKGROUND ART

Conventionally, a scattering estimation method for measurement data of a positron emission tomography apparatus and an image processor are known. Such a scattering estimation method is disclosed in Patent Document 1 and Non-Patent Document 1, for example.

In general, in a positron emission tomography apparatus, noise may be included in an obtained image due to scattering of radiation in a subject during imaging. Therefore, as in Patent Document 1 and Non-Patent Document 1, scattering estimation is performed, and scattering correction is performed on measurement data. As the scattering estimation, a single scattering distribution is estimated on the assumption that radiation is scattered only once in a subject. Furthermore, the radiation scattering includes multiple scattering in which the radiation is scattered a plurality of times in the subject.

Non-Patent Document 1 discloses a method for estimating a multiple scattering distribution modeled as a convolution of a single scattering distribution as a scattering estimation method. That is, in Non-Patent Document 1, a multiple scattering distribution is simulated by convolving a single scattering distribution such that scattering correction is performed.

Patent Document 1 discloses a method for estimating a multiple scattering distribution using a convolution kernel, the amplitude and width of which has been varied, by fitting a single scattering distribution and the multiple scattering distribution by a least square method. That is, in Patent Document 1, scattering correction is performed by directly estimating the multiple scattering distribution.

PRIOR ART

Patent Document

Patent Document 1: U.S. Pat. No. 8,575,554
Non-Patent Document 1: Andrew S. Goggin and John M. Ollinger, "A model for multiple scatters in fully 3D PET", Nuclear Science Symposium and Medical Imaging Conference, 1994., 1994 IEEE Conference Record, Vol. 4, IEEE, 1994, p. 1609-1613

SUMMARY OF THE INVENTION

Problems to be Solved by the Invention

However, convolution function parameters disclosed in Non-Patent Document 1 are parameters determined empirically. Therefore, when the parameters are not appropriate, an error occurs between an estimation result and an actual measurement value. When an error occurs between the estimation result and the actual measurement value, the influence of scattered radiation cannot be sufficiently removed, and noise is generated in an obtained image or excessive scattering correction is performed. Thus, there is an inconvenience that voids occur in the obtained image.

In the scattering estimation method disclosed in Patent Document 1, convolution kernel parameters are determined by fitting the convolution kernel and the multiple scattering distribution. The calculation cost of estimating the multiple scattering distribution by the method of Patent Document 1 is high, and the time required for the scattering estimation disadvantageously becomes longer as compared with the case in which the multiple scattering distribution is simulated from the single scattering distribution.

The present invention is intended to solve the above problem. The present invention aims to provide a scattering estimation method and an image processor each capable of reducing the time required for scattering estimation and capable of significantly reducing or preventing a reduction in image quality due to scattering correction.

Means for Solving the Problems

In order to attain the aforementioned object, as a result of earnest investigations, the inventor has found that when a convolution kernel to be used for scattering estimation is determined, changing the convolution kernel changes a scattered radiation index value, and the resulting image quality changes. Based on this finding, a scattering estimation method according to a first aspect of the present invention includes acquiring positron emission tomography measurement data and absorption coefficient data, generating a radioactive image from the positron emission tomography measurement data and the absorption coefficient data, estimating a single scattering distribution of radiation in the radioactive image from the radioactive image and the absorption coefficient data, determining a convolution kernel for smoothing the single scattering distribution based on a scattered radiation index value of the radioactive image, and fitting, to the positron emission tomography measurement data, a scattering distribution smoothed by applying the convolution kernel to the single scattering distribution. In this specification, the "convolution kernel" refers to a filter function that performs convolution processing, and is synonymous with a "convolution filter". The "radioactive image" refers to an image showing a radiation source in a subject. The "absorption coefficient data" refers to image data indicating the structure in the subject. Therefore, the single scattering distribution of radiation can be estimated from the radioactive image and the absorption coefficient data.

As described above, the scattering estimation method according to the first aspect of the present invention includes the acquiring of the positron emission tomography measurement data and the absorption coefficient data, the generating of the radioactive image, the estimating of the single scattering distribution of radiation in the radioactive image, the determining of the convolution kernel for smoothing the single scattering distribution based on the scattered radiation index value of the radioactive image, and the fitting of, to the positron emission tomography measurement data, the scattering distribution smoothed by applying the convolution kernel to the single scattering distribution. Accordingly, a multiple scattering distribution can be simulated using the single scattering distribution without directly estimating the multiple scattering distribution. Furthermore, the convolution kernel used to smooth the single scattering distribution can be determined not by using a parameter determined empirically but by the scattered radiation index value of the radioactive image. Therefore, the multiple scattering distribution can be simulated from the single scattering distribution using the convolution kernel appropriate for the radioactive image, and thus it is possible to significantly reduce or prevent the occurrence of an error between an estimation result and an actual measurement value. Consequently, it is possible to reduce the time required for the scattering estimation and to significantly reduce or prevent a reduction in image quality due to scattering correction.

In the aforementioned scattering estimation method according to the first aspect, the scattered radiation index value is preferably a scatter fraction, and the determining of the convolution kernel preferably includes determining the convolution kernel based on a result of comparison between scatter fractions of radioactive images smoothed using a plurality of parameters that characterize the convolution kernel. The inventor has found that changes of the images occurring when a parameter of the convolution kernel is varied are based on changes of the scatter fractions. Furthermore, the inventor application has found that an appropriate parameter of the convolution kernel can be easily determined by comparing the scatter fractions. Therefore, with such a configuration, the scatter fractions of the radioactive images smoothed by varying the parameter of the convolution kernel are compared such that the convolution kernel can be easily determined.

In this case, the determining of the convolution kernel preferably includes determining the convolution kernel based on magnitudes of changes of the scatter fractions with changes of the plurality of parameters. The inventor has found that when the changes of the scatter fractions with the changes of the parameters of the convolution kernel are large, noise in the obtained image is reduced. Therefore, with such a configuration, the convolution kernel can be determined more easily.

In the aforementioned scattering estimation method according to the first aspect, the estimating of the single scattering distribution from the radioactive image and the absorption coefficient data preferably includes estimating the single scattering distribution by a single scattering simulation method. Accordingly, the single scattering distribution of radiation can be easily estimated from the radioactive image and the absorption coefficient data. The single scattering simulation method refers to a method for estimating the scattering distribution in the subject from the radioactive image and the absorption coefficient data.

In the aforementioned scattering estimation method according to the first aspect, the estimating of the single scattering distribution from the radioactive image and the absorption coefficient data preferably includes estimating the single scattering distribution by a Monte Carlo simulation method. Even with such a configuration, the single scattering distribution of radiation can be easily estimated similarly to the case in which the single scattering distribution is estimated using the single scattering simulation method. The Monte Carlo simulation is a method for obtaining an approximate solution by repeating a simulation using random numbers.

In the aforementioned scattering estimation method according to the first aspect, the convolution kernel preferably defines a weight distribution specified by a parameter relating to dispersion, and the smoothing of the single scattering distribution is preferably performed by a weighted average filter using the convolution kernel. With such a configuration, using the convolution kernel in which the weight distribution is changed by the parameter relating to dispersion, the multiple scattering distribution of radiation can be simulated from the single scattering distribution of radiation. Consequently, as compared with the case in which the multiple scattering distribution is directly estimated, the processing time can be reduced. In addition, the parameter of the convolution kernel is determined using actually measured data, and thus the multiple scattering distribution can be simulated using an appropriate convolution kernel as compared with a method for empirically determining the parameter. Consequently, the accuracy of scattering correction can be improved.

An image Processor according to a second aspect of the present invention includes a controller and an image data acquirer configured to acquire positron emission tomography measurement data and absorption coefficient data. The controller is configured to generate a radioactive image from the positron emission tomography measurement data and the absorption coefficient data, estimate a single scattering distribution from the radioactive image and the absorption coefficient data, determine a convolution kernel for smoothing the single scattering distribution based on a scattered radiation index value of the radioactive image, and fit, to the positron emission tomography measurement data, a scattering distribution smoothed by applying the convolution kernel to the single scattering distribution.

As described above, the image processor according to the second aspect of the present invention includes the controller and the image data acquirer, and the controller is configured to generate the radioactive image from the positron emission tomography measurement data and the absorption coefficient data, estimate the single scattering distribution from the radioactive image and the absorption coefficient data, determine the convolution kernel for smoothing the single scattering distribution based on the scattered radiation index value of the radioactive image, and fit, to the positron emission tomography measurement data, the scattering distribution smoothed by applying the convolution kernel to the single scattering distribution. Accordingly, a multiple scattering distribution can be simulated using the single scattering distribution without directly estimating the multiple scattering distribution. Furthermore, the convolution kernel used to smooth the single scattering distribution can be determined not by using a parameter determined empirically but by the scattered radiation index value of the radioactive image. Therefore, the multiple scattering distribution can be simulated from the single scattering distribution using the convolution kernel appropriate for the radioactive image, and thus it is possible to significantly reduce or prevent the occurrence of an error between an estimation result and an actual measurement value. Consequently, it is possible to reduce the time required for the scattering estimation and to significantly reduce or prevent a reduction in image quality due to scattering correction.

Effect of the Invention

According to the present invention, as described above, it is possible to provide the scattering estimation method and the image processor each capable of reducing the time required for the scattering estimation and capable of significantly reducing or preventing a reduction in image quality due to the scattering correction.

BRIEF DESCRIPTION OF THE DRAWINGS

FIGS. 7(D) and (E) are diagrams for illustrating the method for determining the convolution kernel according to the embodiment of the present invention.

MODES FOR CARRYING OUT THE INVENTION

An embodiment embodying the present invention is hereinafter described on the basis of the drawings.
(Configuration of Image Processor)

The configuration of a positron emission tomography system 100 including an image processor 2 according to this embodiment is now described with reference to FIGS. 1 to 3.

Figure 1:
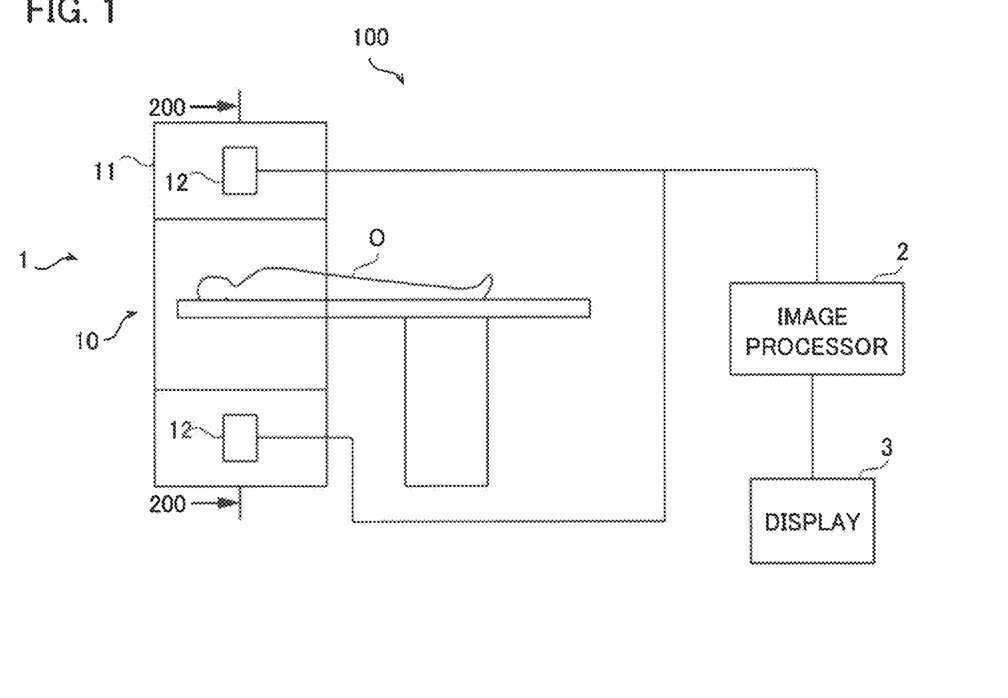
FIG. 1 is a block diagram showing the overall configuration of a positron emission tomography system including an image processor according to an embodiment of the present invention.

As shown in FIG. 1, the positron emission tomography system 100 includes a positron emission tomography apparatus 1, the image processor 2, and a display 3.

The positron emission tomography apparatus 1 is provided with an imaging unit 10. In addition, the imaging unit 10 includes a housing 11.

The positron emission tomography apparatus 1 includes a plurality of detectors 12. Specifically, the plurality of detectors 12 are disposed inside the housing 10. The plurality of detectors 12 are disposed in such a manner as to surround a subject O. Each of the detectors 12 detects radiation emitted from the subject O. Each of the detectors 12 is configured to convert the detected radiation into an electrical signal and transmit the electrical signal to a controller 20. In this embodiment, a radiolabeling reagent is administered to the subject O in advance, and each of the detectors 12 detects the radiation emitted from the subject O. The radiolabeling reagent is 18F-FDG (fluorodeoxyglucose), for example.

Figure 2:
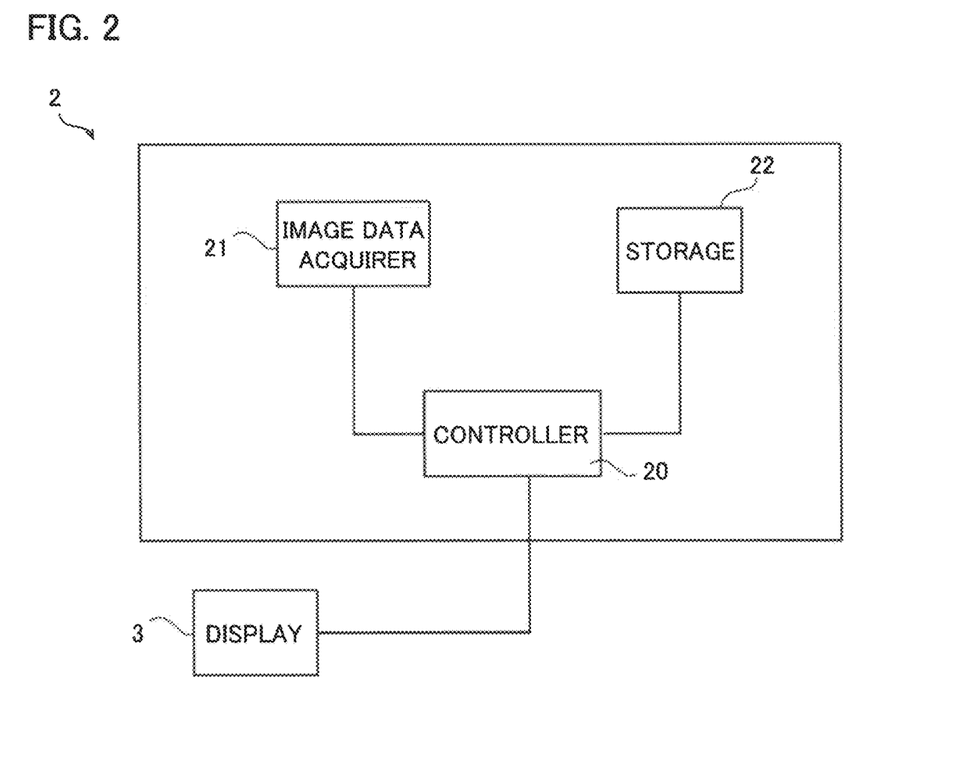
FIG. 2 is a block diagram showing the overall configuration of the image processor according to the embodiment of the present invention.

FIG. 2 is a block diagram showing the overall configuration of the image processor 2. As shown in FIG. 2, the image processor 2 includes the controller 20, an image data acquirer 21 that acquires positron emission tomography measurement data and absorption coefficient data, and a storage 22.

The controller 20 is configured to generate a radioactive image 5 (see FIG. 8) from the positron emission tomography measurement data and the absorption coefficient data acquired by the image data acquirer 21. The controller 20 is configured to estimate a single scattering distribution from the generated radioactive image 5 and the absorption coefficient data. The controller 20 is configured to simulate a multiple scattering distribution from the estimated single scattering distribution. The controller 20 includes a central processing unit (CPU), a graphics processing unit (GPU), etc. The configuration in which the controller 20 performs scattering estimation is now described below.

The image data acquirer 21 is configured to acquire the positron emission tomography measurement data acquired by the positron emission tomography apparatus 1 and the absorption coefficient data obtained by converting form data of the subject O acquired by a tomography apparatus (CT apparatus) or the like. As the absorption coefficient data, data obtained by converting data acquired by a magnetic resonance imaging apparatus (MRI apparatus) may be used.

The storage 22 is configured to store a program etc. used when the controller 20 performs radiation scattering estimation. The storage 22 includes a hard disk drive (HDD) etc.

The display 3 is configured to display the radioactive image 5 generated by the controller 20. The display 3 includes a liquid crystal monitor, for example.

Figure 3:
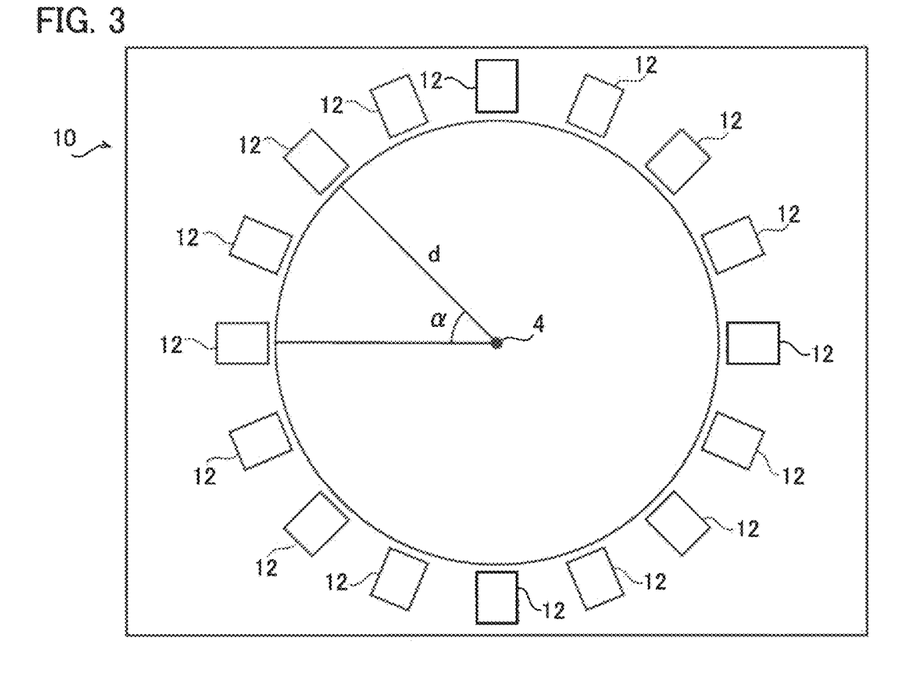
FIG. 3 is a block diagram of a positron emission tomography apparatus according to the embodiment of the present invention.

FIG. 3 is a sectional view of the housing 11 of the positron emission tomography apparatus 1, taken along the line 200-200 in FIG. 1. As shown in FIG. 3, the detectors 12 are disposed circumferentially inside the housing 11. A pair of radiation rays emitted in opposite directions from a radiation source of the subject O are detected by a pair of detectors 12 that face each other with the radiation source interposed therebetween. In FIG. 3, for the sake of convenience, the center of a virtual circle along which the detectors 12 are disposed is shown as a center 4. In FIG. 3, the radius of the virtual circle is shown as d. In FIG. 3, an angle between the center 4 and the detectors 12 is shown as a.

Figure 4:
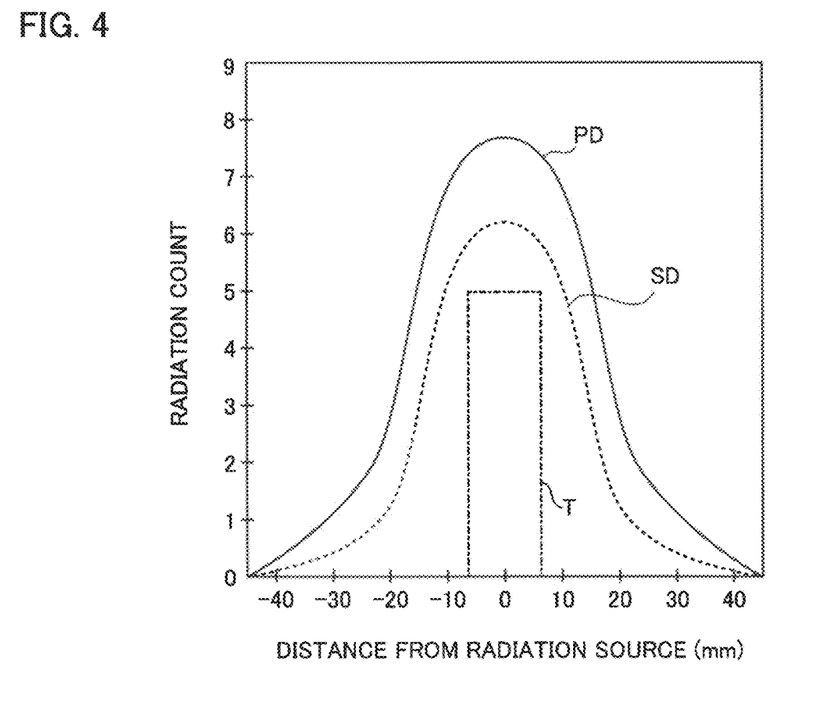
FIG. 4 is a schematic view for illustrating the distribution of radiation detected by a detector according to the embodiment of the present invention.

FIG. 4 is a graph PD, a graph SD, and a graph T showing radiation counts (radiation intensities) detected by the detectors 12. In the graphs of FIG. 4, the horizontal axis represents a distance from the radiation source, and the vertical axis represents a radiation count. The graph PD is a graph showing the relationship between the radiation count detected by the detectors 12 and the distance from the radiation source. The graph SD is a graph showing the relationship between the radiation count derived from scattered radiation among the radiation detected by the detectors 12 and the distance from the radiation source. The graph T is a graph obtained by removing the graph SD from the graph PD. In other words, the graph T is a graph showing the relationship between a radiation count obtained by removing the scattered radiation among the radiation detected by the detectors 12 and the distance from the radiation source.

The radiation is scattered by the tissue or the like inside the subject O when passing through the subject O, and thus the distribution of the radiation actually detected by the detectors 12 is shown in the graph PD in which the graph T and the graph SD are combined. Therefore, in order to obtain the radiation emitted from the subject O, it is necessary to perform scattering correction for removing the scattered radiation as shown in the graph SD from signals detected by the detectors 12.

The scattered radiation includes a single scattered radiation that has been scattered once by the tissue or the like inside the subject O, and a multiple scattered radiation that has been scattered a plurality of times inside the subject O. In this embodiment, the controller 20 estimates a single scattering distribution from the radioactive image 5 and the absorption coefficient data by a single scattering simulation method. Thereafter, the controller 20 is configured to perform the scattering correction by estimating a scattering distribution (graph SD) taking into account the multiple scattering distribution from the estimated single scattering distribution. The single scattering simulation method is a method for estimating the scattering distribution (graph SD) inside the subject O from the radioactive image 5 and the absorption coefficient data.

(Scattering Estimation Method)

A scattering estimation method in this embodiment is now described with reference to FIGS. 5 to 9.

Figure 5:
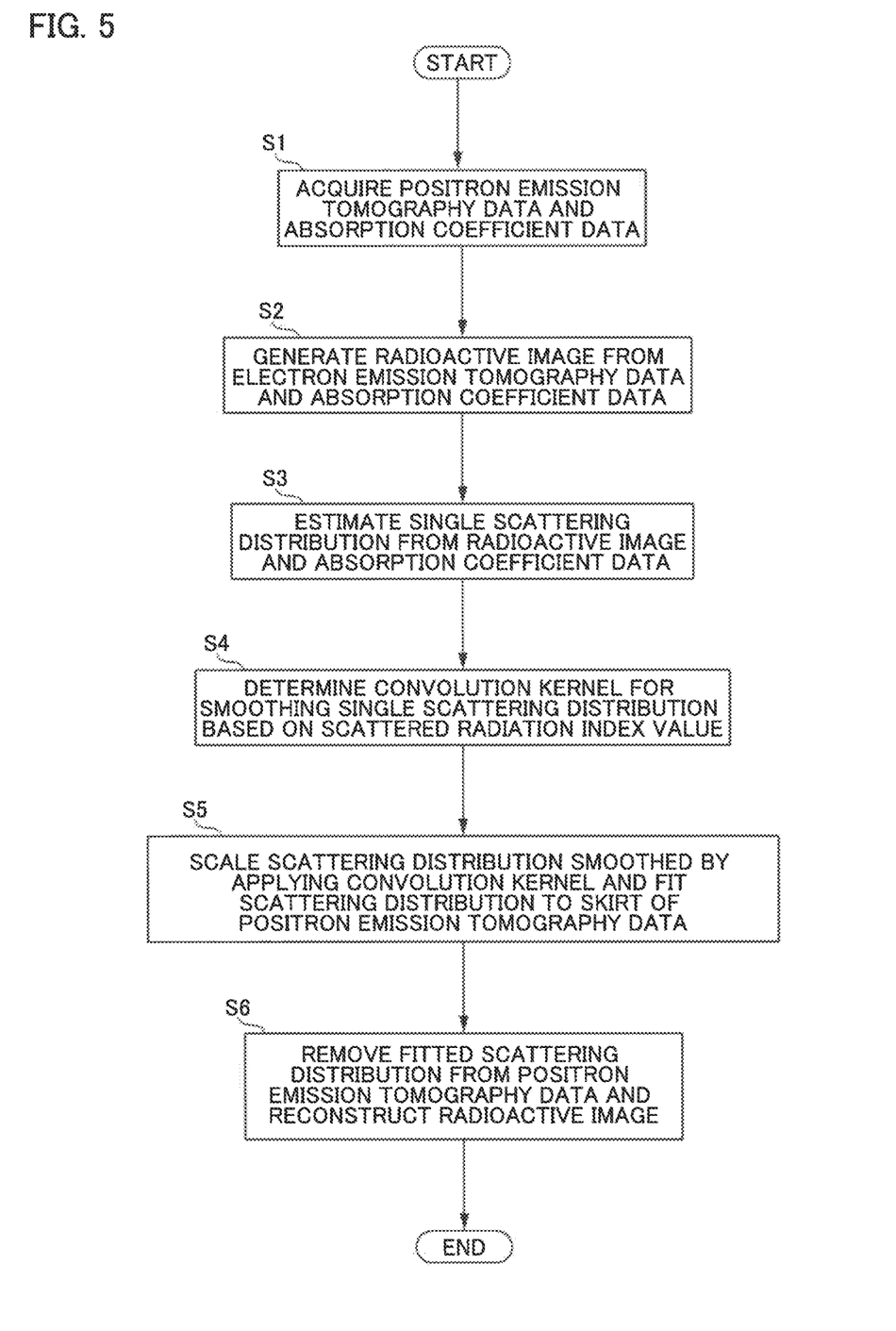
FIG. 5 is a flowchart for illustrating a scattering estimation method according to the embodiment of the present invention.

First, the flow of the scattering estimation method in this embodiment is described with reference to FIG. 5.

In step S1, the image data acquirer 21 acquires the positron emission tomography measurement data and the absorption coefficient data. As a data format to be acquired, any format of data such as a list data format and a sinogram format may be used. Data to be used may be two-dimensional data or three-dimensional data.

Next, in step S2, the controller 20 generates the radioactive image 5 from the positron emission tomography measurement data and the absorption coefficient data. Any method may be used as a method for generating the radioactive image 5. For example, the controller 20 is configured to generate the radioactive image 5 using a reconstruction technique (FBP), a successive approximation reconstruction technique (OSEM, MLEM), or the like. The controller 20 is configured to apply at least sensitivity correction, random coincidence correction, and absorption correction when generating the radioactive image 5. The random coincidence correction is performed using a known technique such as a delayed coincidence method or an estimation method based on single counting. The controller 20 is configured to perform noise reduction processing when generating the radioactive image 5. As the noise reduction processing, a Gaussian filter or a non-local means filter may be applied, for example. The noise reduction processing may be performed at any timing of pre-processing applied to projection data, processing during reconstruction, and post-processing after reconstruction. Next, the processing advances to step S3.

In step S3, the controller 20 estimates the single scattering distribution from the generated radioactive image 5 and the acquired absorption coefficient data. Next, in step S4, a convolution kernel for smoothing the single scattering distribution is determined based on a scattered radiation index value SF of the radioactive image 5. Note that the scattered radiation index value SF of the radioactive image 5 refers to a proportion of radiation derived from scattered radiation to all radiation detected by the detectors 12, and is specifically a scatter fraction RF.

Next, in step S5, the scattering distribution (graph SD) smoothed by applying the convolution kernel to the single scattering distribution is scaled and is fitted to a skirt of the positron emission tomography measurement data. In the scaling method, threshold processing is performed on an absorption coefficient sinogram generated from the absorption coefficient data (absorption coefficient images) to determine regions inside and outside an object. Thereafter, a region of interest (ROI) is set in the region outside the object, and a count in the ROI is determined to match the measurement data. In addition, the scaling is performed for each slice, but may not be performed for each slice.

Next, in step S6, the fitted scattering distribution (graph SD) is removed from the positron emission tomography data, and the radioactive image 5 is reconstructed.

(Method for Determining Convolution Kernel)

Figure 6:
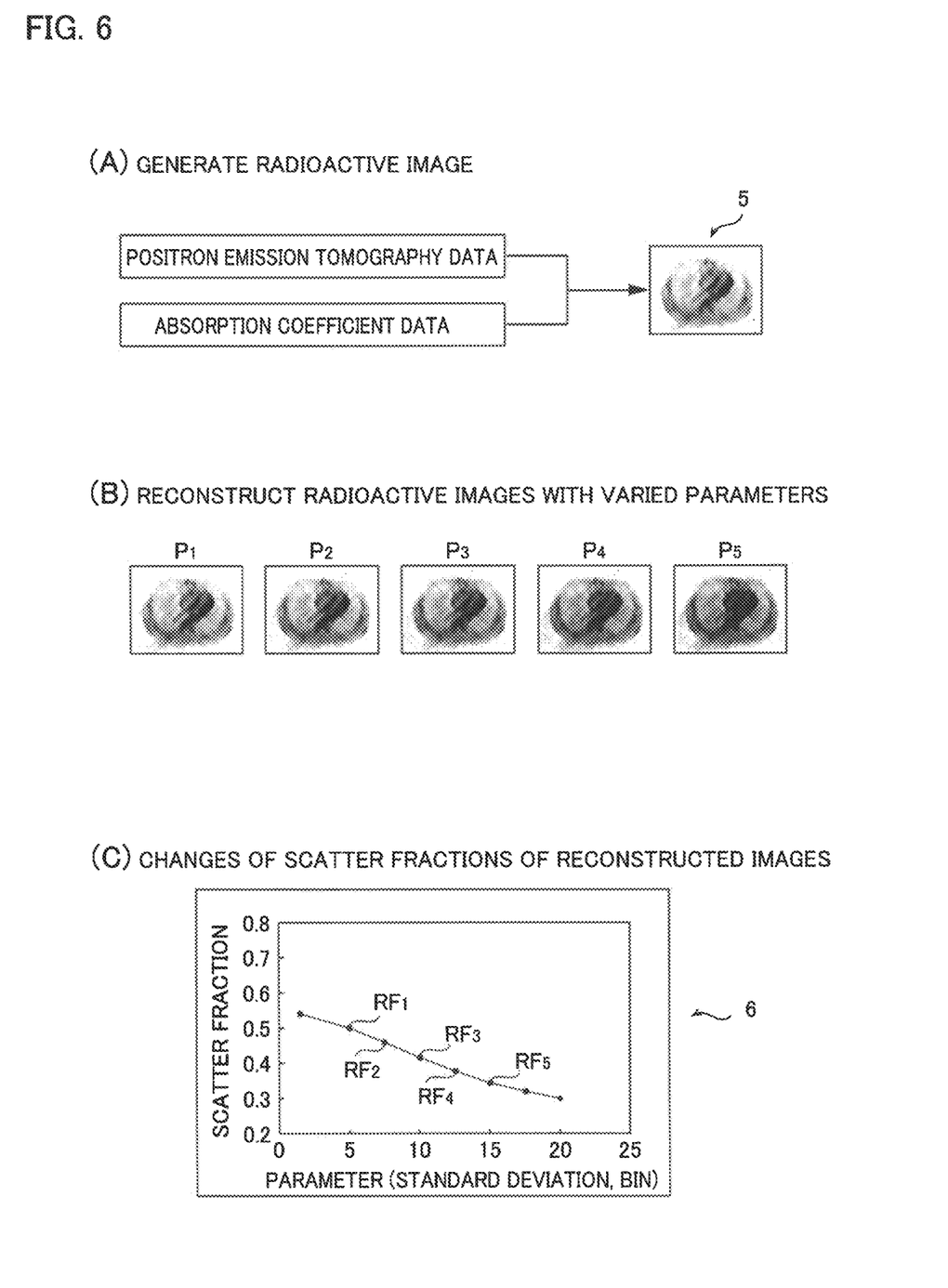
FIGS. 6(A) to 6(C) are diagrams for illustrating a method for determining a convolution kernel according to the embodiment of the present invention.
Figure 7:
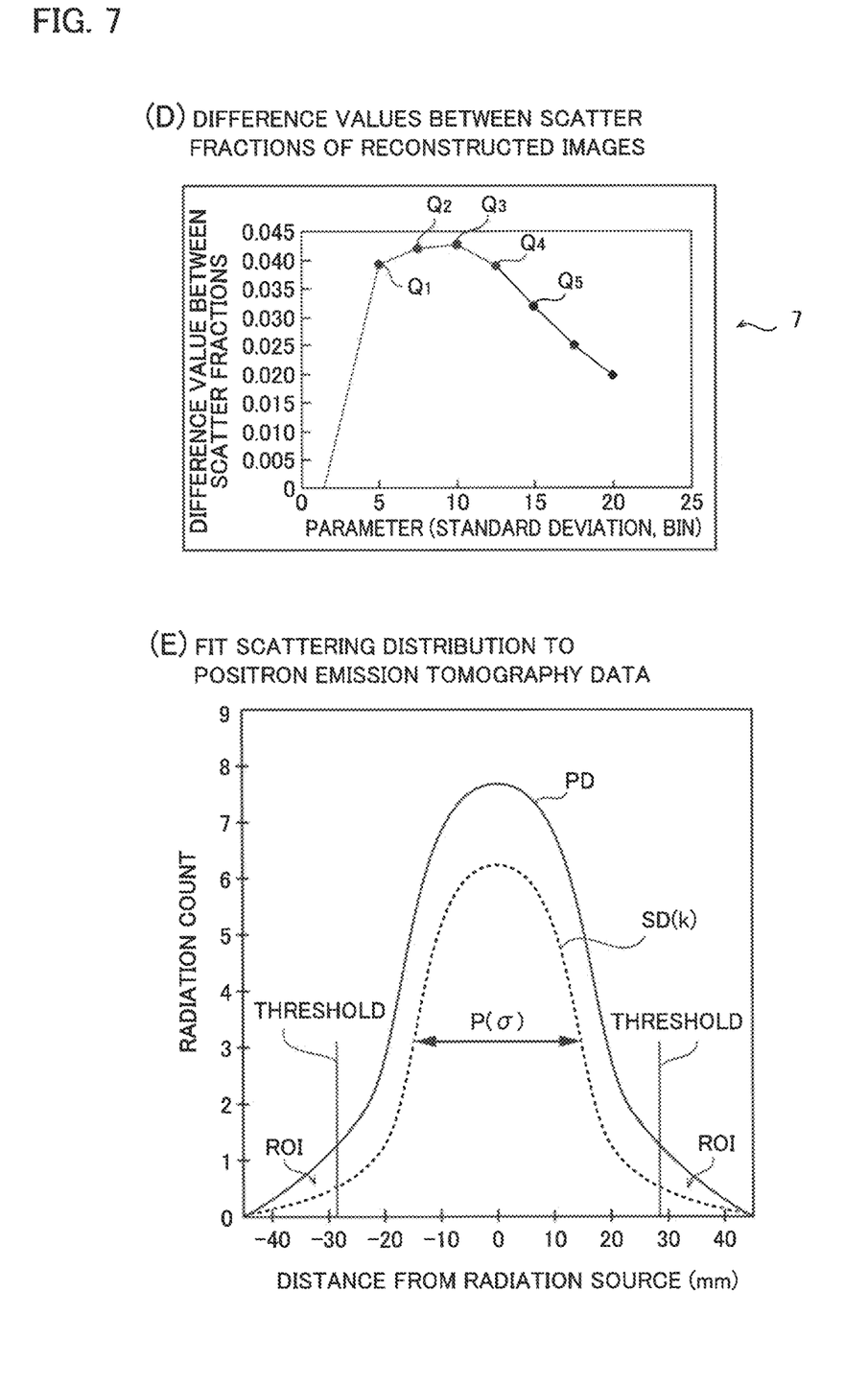

A method in which the controller 20 determines the convolution kernel is now described with reference to FIGS. 6 and 7.

As shown in FIG. 6(A), in this embodiment, the controller 20 generates the radioactive image 5 from the positron emission tomography data and absorption coefficient data. The controller 20 is configured to estimate single scattering of the radioactive image 5 from the generated radioactive image 5 by the single scattering simulation method.

Specifically, the controller 20 is configured to perform the scattering correction using the scattering distribution (graph SD) modeled by the following formula (1).

$$S(r,\theta,z) = \int S_s(r-u,\theta,z)k(r)du \quad (1)$$

where S represents a scattering distribution (graph SD) taking into account multiple scattering, $S_s$ represents a single scattering distribution, r represents a number representing the order of the detectors 12 in the radial direction, $\theta$ represents a number representing the order in the angular direction in which the detectors 12 are disposed, z represents a number representing the order in the slice direction, i.e. z represents a number representing the order of images captured when the subject O is stepped in the body axis direction of the subject O, and k represents a convolution kernel.

In this embodiment, the convolution kernel defines a weight distribution specified by a parameter P (see FIG. 7(E)) relating to dispersion. Smoothing of the single scattering distribution is performed by a weighted average filter using the convolution kernel. That is, in this embodiment, the controller 20 is configured to smooth the single scattering distribution using the weighted average filter as the convolution kernel, and obtain the scattering distribution (graph SD) taking into account the multiple scattering distribution. The weighted average filter is a Gaussian function (Gaussian filter), and is expressed by the following formula (2), for example.

[Formula 2]

$$k(r) = \frac{1}{\sqrt{2\pi}\,\sigma} \exp(-r^2/2\sigma^2) \quad (2)$$

where $\sigma$ represents a standard deviation of the Gaussian function.

In this embodiment, the controller 20 determines the convolution kernel based on the results of comparison between the scatter fractions RF of radioactive images 5 smoothed using a plurality of parameters P characterizing the convolution kernel. Specifically, the controller 20 determines the convolution kernel based on the magnitudes of changes of the scatter fractions RF with changes of the plurality of parameters P. In this embodiment, the parameters P characterizing the convolution kernel are $\sigma$ in the above formula (2). The parameters P are the standard deviation ($\sigma$) of the graph SD shown in FIG. 7(E).

The controller 20 is configured to reconstruct a plurality of radioactive images 5 by applying a convolution kernel in which the parameter P has been varied to the single scattering distribution. Specifically, as shown in FIG. 6(B), the controller 20 reconstructs the plurality of radioactive images 5 using the convolution kernel to which parameters $P_1$ to $P_5$ have been applied. In this embodiment, the parameters $P_1$ to $P_5$ are set in such a manner as to increase at predetermined value intervals. It is known that the multiple scattering is distributed in a wider range than the single scattering, and thus the parameter $P_1$ is preferably set to a value larger than a parameter P of a convolution kernel in the case in which smoothing is not performed.

The controller 20 is configured to obtain the scatter fraction RF from the adjacent radioactive images 5. The scatter fraction RF refers to a value indicating a proportion of radiation derived from scattered radiation to all radiation detected by the detectors 12, and can be obtained by the following formula (3).

[Formula 3]

$$SF_i = \frac{S_i}{P_c - RD} \quad (3)$$

where i represents a number indicating the order of smoothing parameter P, $S_i$ represents an estimated scatter coincidence, $P_c$ represents measured prompt coincidence data, and RD represents random count data.

FIG. 6(C) shows a graph 6 in which the scatter fractions of the radioactive images 5 reconstructed with the parameters P set to $P_1$ to $P_5$ are plotted. The horizontal axis of the graph 6 represents a parameter value (bin value), and the vertical axis of the graph 6 represents a scatter fraction. As shown in FIG. 6(C), the controller 20 is configured to generate the graph 6 in which the scatter fractions $RF_1$ to $RF_5$ are plotted. The scatter fractions $RF_1$ to $RF_5$ in FIG. 6(C) are values of the scatter fractions RF of the radioactive images 5 reconstructed with the parameters $P_1$ to $P_5$, respectively. As shown in FIG. 6(C), it can be seen that as the parameter P increases, the scatter fraction RF decreases. In addition, the length of a bin is about 8 mm.

The controller 20 is configured to take difference values Q between the scatter fractions RF and create a graph 7 shown in FIG. 7(D). In addition, the difference values Q between the scatter fractions RF are values obtained by taking differences between the scatter fractions RF corresponding to smaller numbers representing the order of the parameters P (i in the above formula (1)) and the scatter fractions RF corresponding to larger numbers representing the order of the parameters P among the adjacent scatter fractions RF, and can be obtained by the following formula (4).

$$dSF_i = SF_{i-1} - SF_i \quad (4)$$

where $dSF_i$ represents a difference value Q between scatter fractions RF.

As shown in the graph 7 of FIG. 7(D), the difference values Q between the scatter fractions RF are shown as a graph that is convex upward. The controller 20 is configured to set the parameter P at a time when the difference value Q between the scatter fractions RF is maximum (local maximum) as a parameter P(σ) to be applied to the convolution kernel. When the number of parameters P is too large, differences between the difference values Q between the scatter fractions RF become small, and it may be difficult to select an appropriate parameter P due to noise or the like. When the number of parameters P is too small, a range in which the difference value Q between the scatter fractions RF is actually maximum is not included, and there is a possibility that an appropriate parameter P cannot be selected. Therefore, although the number of parameters P varies somewhat depending on the size of the subject O, it is preferable to set the number of parameters P to about five in general.

As shown in FIG. 7(E), the controller 20 is configured to scale the scattering distribution (graph SD) smoothed by applying the convolution kernel to the single scattering distribution, and fit the scattering distribution to the skirt of the positron emission tomography measurement data. Specifically, the controller 20 performs the threshold processing on the measurement data, and determines the regions inside and outside the object. Thereafter, the controller 20 is configured to set the region of interest (ROI) in the region outside the object, scale the scattering distribution (graph SD) such that the count in the ROI matches the measurement data, and fit the scattering distribution to the skirt of the positron emission tomography measurement data.

The controller 20 is configured to remove the fitted scattering distribution (graph SD) from the positron emission tomography data and reconstruct the radioactive images 5.

An example in which a finding about a method for determining the optimum parameter P of the convolution kernel in this embodiment has been obtained is described below.

FIRST EXAMPLE

An experiment conducted to determine a parameter P characterizing a convolution kernel according to a first example is now described with reference to FIG. 8.

In the first example, the parameter P was varied to perform scattering correction on radioactive images 5 obtained by imaging an abdomen such that a plurality of radioactive images 5 were reconstructed, and the plurality of radioactive images 5 were compared such that the optimum convolution kernel was determined.

FIG. 8(A) is a diagram showing the radioactive images 5 that have been subjected to scattering correction by changing the parameter of the convolution kernel at the time of imaging the abdomen so as to be reconstructed. Images shown in a row (D) in FIG. 8(A) are abdominal axial (body axial cross-section) images, and images shown in a row (E) are abdominal coronal (coronal cross-section) images. FIG. 8(B) is a graph 6 showing changes of the scatter fractions of the radioactive images 5 occurring when the parameter of the convolution kernel is varied. In FIG. 8(B), the horizontal axis represents the parameter of the convolution kernel, and the vertical axis represents the scatter fraction. FIG. 8(C) is a graph 7 showing difference values between the scatter fractions occurring when the parameter P of the convolution kernel is varied. In FIG. 8(C), the horizontal axis represents the parameter of the convolution kernel, and the vertical axis represents the difference value between the scatter fractions.

In the first example, as shown in FIG. 8(A), the radioactive images 5 were reconstructed with the parameter P set to no smoothing, 5.0 bins, 7.5 bins, 10 bins, 15 bins, and 20 bins. The term "no smoothing" refers to setting the parameter P to 1.5 bins to perform scattering correction.

In the example shown in FIG. 8(A), the radioactive images 5 reconstructed with the parameter P set to no smoothing, 5.0 bins, and 7.5 bins were subjected to excessive scattering correction, and the image outlines were blurred or voids occurred in the images. In addition, the radioactive images 5 reconstructed with the parameter P set to 15 bins and 20 bins could not be subjected to sufficient scattering correction, and noise was generated in the images.

When the scatter fraction RF was obtained from each of the radioactive images 5, the relationship as shown in FIG. 8(B) was obtained. Moreover, the difference values Q between the scatter fractions RF were taken, and the graph 7 as shown in FIG. 8(C) was created.

When the radioactive images 5 were compared based on the graph 7 shown in FIG. 8(C) and the radioactive images 5 shown in FIG. 8(A), it has been found that the quality of the radioactive image 5 increases as the difference value Q between the scatter fractions RF increases, and the image quality is the best when the difference value Q between the scatter fractions RF is maximized.

Figure 8:
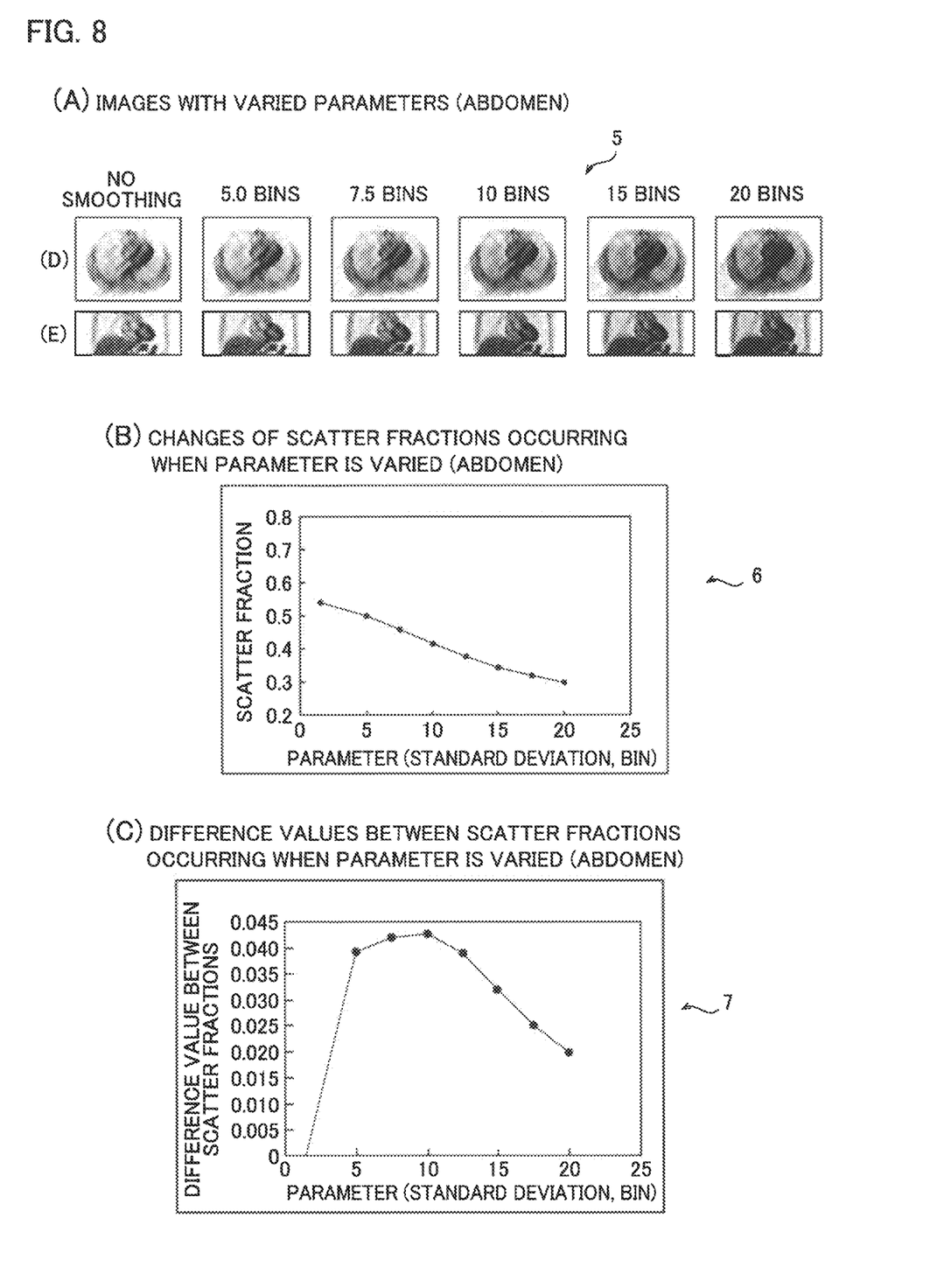
FIG. 8(A) is a diagram showing images of an abdomen for illustrating a scattering estimation method according to a first example of the embodiment of the present invention.
FIG. 8(B) is a diagram showing scatter fractions of the images of the abdomen.
FIG. 8(C) is a diagram showing difference values between the scatter fractions of the images of the abdomen.

In the first example, as shown in FIG. 8, when the parameter P was set to 10 bins, the image outline was clearly displayed, no void was found, and there was little noise. That is, in the first example, the result that the image quality was the best when the parameter P was set to 10 bins was obtained.

SECOND EXAMPLE

An experiment conducted to determine a parameter P characterizing a convolution kernel according to a second example is now described with reference to FIG. 9.

In the second example, the parameter P characterizing the optimum convolution kernel was obtained from radioactive images 50 of a pelvis by the same method as in the first example.

FIG. 9(A) is a diagram showing the radioactive images 50 that have been subjected to scattering correction by changing the parameter P of the convolution kernel at the time of imaging the pelvis so as to be reconstructed. Images shown in a row (D) in FIG. 9(A) are pelvic axial (body axial cross-section) images, and images shown in a row (E) are pelvic coronal (coronal cross-section) images. FIG. 9(B) is a graph 60 showing changes of the scatter fractions of the radioactive images 50 occurring when the parameter of the convolution kernel is varied. In FIG. 9(B), the horizontal axis represents the parameter of the convolution kernel, and the vertical axis represents the scatter fraction. FIG. 9(C) is a graph 70 showing difference values between the scatter fractions occurring when the parameter of the convolution kernel is varied. In FIG. 9(C), the horizontal axis represents the parameter of the convolution kernel, and the vertical axis represents the difference value between the scatter fractions.

In the second example, as shown in FIG. 9(A), the radioactive images 50 were reconstructed with the parameter P set to no smoothing (1.5 bins), 5.0 bins, 7.5 bins, 10 bins, 15 bins, and 20 bins.

Figure 9:
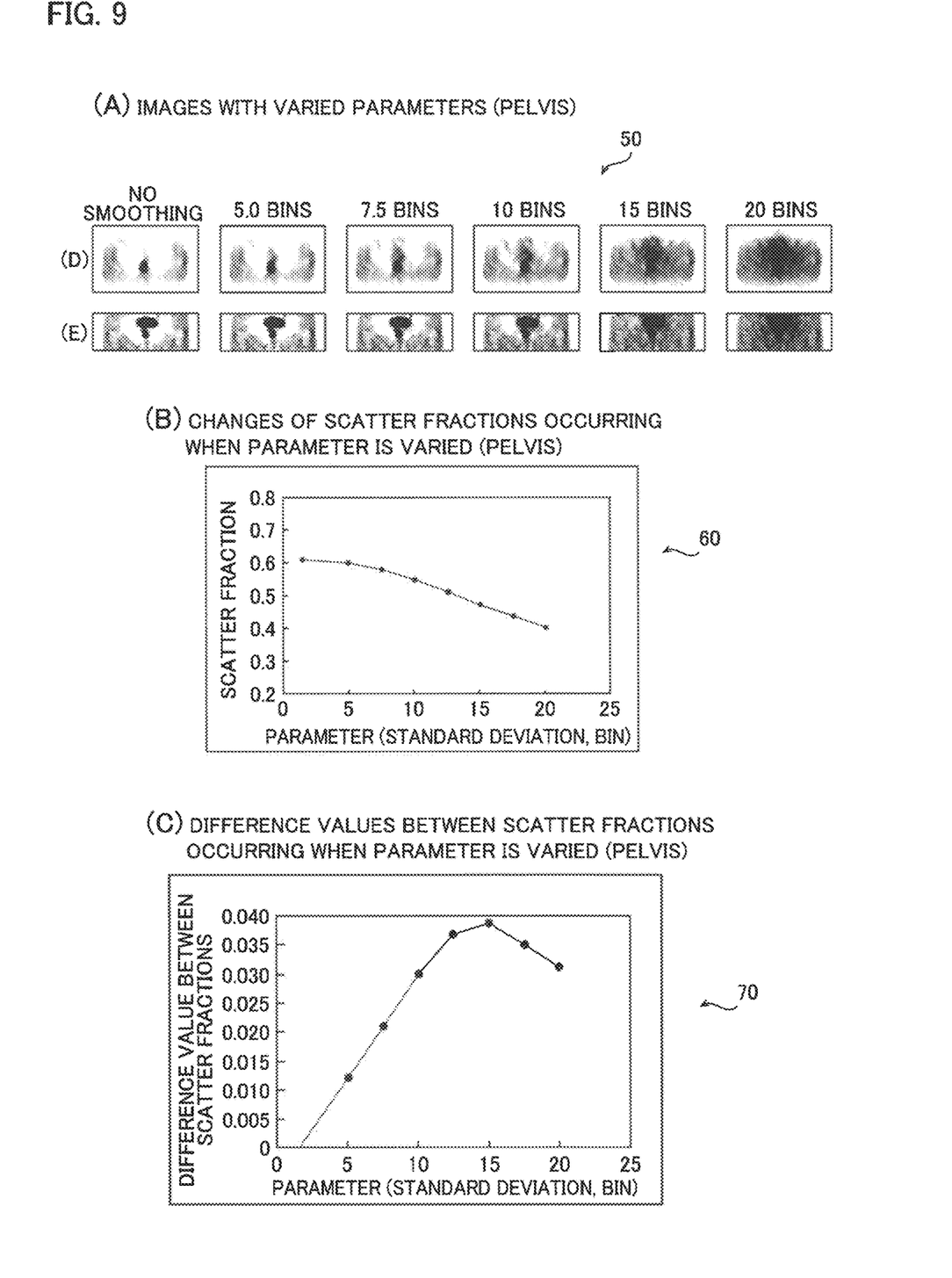
FIG. 9(A) is a diagram showing images of a pelvis for illustrating a scattering estimation method according to a second example of the embodiment of the present invention.
FIG. 9(B) is a diagram showing scatter fractions of the images of the pelvis.
FIG. 9(C) is a diagram showing difference values between the scatter fractions of the images of the pelvis.

In the second example, as shown in FIG. 9, the radioactive images 50 reconstructed with the parameter P set to no smoothing (1.5 bins), 5.0 bins, 7.5 bins, and 10 bins were subjected to excessive scattering correction, and voids occurred in the images. In addition, the radioactive image 5 reconstructed with the parameter P set to 20 bins could not be subjected to sufficient scattering correction, and noise was generated in the image. In the example shown in FIG. 9, when the parameter P was set to 15 bins, no void was found, and there was little noise. That is, in the second example, the result that the image quality was the best when the parameter P was set to 15 bins was obtained.

In addition to the above examples, a total of twenty experiments were conducted. In any experiment, the result that the quality of the radioactive image 5 obtained with the parameter P at which the difference value Q between the scatter fractions RF was maximized was the best was obtained.

Advantages of Embodiment

In the embodiment of the present invention, the following advantages are obtained.

In this embodiment, as described above, the scattering estimation method includes acquiring the positron emission tomography measurement data and the absorption coefficient data, generating the radioactive image 5 (radioactive image 50) from the positron emission tomography measurement data and the absorption coefficient data, estimating the single scattering distribution of the radiation in the radioactive image 5 (radioactive image 50) from the radioactive image 5 (radioactive image 50) and the absorption coefficient data, determining the convolution kernel for smoothing the single scattering distribution based on the scattered radiation index value SF of the radioactive image 5 (radioactive image 50), and fitting, to the positron emission tomography measurement data, the scattering distribution (graph SD) smoothed by applying the convolution kernel to the single scattering distribution. Accordingly, the multiple scattering distribution can be simulated using the single scattering distribution without directly estimating the multiple scattering distribution. Furthermore, the convolution kernel used to smooth the single scattering distribution can be determined not by using the parameter P determined empirically but by the scattered radiation index value SF of the radioactive image 5 (radioactive image 50). Therefore, the multiple scattering distribution can be simulated from the single scattering distribution using the convolution kernel appropriate for the radioactive image 5 (radioactive image 50). Consequently, it is possible to reduce the time required for the scattering estimation and to significantly reduce or prevent a reduction in image quality due to the scattering correction.

In this embodiment, as described above, the scattered radiation index value SF is the scatter fraction RF, and the determining of the convolution kernel includes determining the convolution kernel based on the results of comparison between the scatter fractions RF of the radioactive images 5 (radioactive images 50) smoothed using the plurality of parameters P characterizing the convolution kernel. Accordingly, the scatter fractions RF of the radioactive images 5 (radioactive images 50) smoothed by changing the parameter P of the convolution kernel are compared such that the convolution kernel can be easily determined.

In this embodiment, as described above, the convolution kernel is determined based on the magnitudes of changes of the scatter fractions RF with changes of the plurality of parameters P. Accordingly, the convolution kernel can be determined more easily.

In this embodiment, as described above, the estimating of the single scattering distribution from the radioactive image 5 (radioactive image 50) and the absorption coefficient data includes estimating the single scattering distribution by the single scattering simulation method. Accordingly, the single scattering distribution of the radiation can be easily estimated from the radioactive image 5 (radioactive image 50) and the absorption coefficient data.

In this embodiment, as described above, the convolution kernel defines the weight distribution specified by the parameter P relating to dispersion, and smoothing of the single scattering distribution is performed by the weighted average filter using the convolution kernel. Accordingly, using the convolution kernel in which the weight distribution is changed by the parameter P relating to dispersion, the multiple scattering distribution of the radiation can be simulated from the single scattering distribution of the radiation. Consequently, as compared with the case in which the multiple scattering distribution is directly estimated, the processing time can be reduced. In addition, the parameter P of the convolution kernel is determined using actually measured data, and thus the multiple scattering distribution can be simulated using an appropriate convolution kernel as compared with a method for empirically determining the parameter P. Consequently, the accuracy of scattering correction can be improved.

In this embodiment, as described above, the image processor 2 includes the controller 20 and the image data acquirer 21 configured to acquire the positron emission tomography measurement data and the absorption coefficient data. The controller 20 is configured to generate the radioactive image 5 (radioactive image 50) from the positron emission tomography measurement data and the absorption coefficient data, estimate the single scattering distribution from the radioactive image 5 (radioactive image 50) and the absorption coefficient data, determine the convolution kernel for smoothing the single scattering distribution based on the scattered radiation index value SF of the radioactive image 5 (radioactive image 50), and fit, to the positron emission tomography measurement data, the scattering distribution (graph SD) smoothed by applying the convolution kernel to the single scattering distribution. Accordingly, the multiple scattering distribution can be simulated using the single scattering distribution without directly estimating the multiple scattering distribution. Furthermore, the convolution kernel used to smooth the single scattering distribution can be determined not by using the parameter P determined empirically but by the scattered radiation index value SF of the radioactive image 5 (radioactive image 50). Therefore, the multiple scattering distribution can be simulated from the single scattering distribution using the convolution kernel appropriate for the radioactive image 5 (radioactive image 50).

Consequently, it is possible to reduce the time required for the scattering estimation and to significantly reduce or prevent a reduction in image quality due to the scattering correction.

MODIFIED EXAMPLES

The embodiment and examples disclosed this time must be considered as illustrative in all points and not restrictive. The scope of the present invention is not shown by the above description of the embodiment and examples but by the scope of claims for patent, and all modifications (modified examples) within the meaning and scope equivalent to the scope of claims for patent are further included.

For example, while in the estimating of the single scattering distribution from the radioactive image 5 (radioactive image 50) and the absorption coefficient data, the single scattering distribution is estimated by the single scattering simulation method in the aforementioned embodiment, the present invention is not limited to this. For example, in the estimating of the single scattering distribution from the radioactive image 5 (radioactive image 50) and the absorption coefficient data, the single scattering distribution may be estimated by a Monte Carlo simulation method. Even with such a configuration, the single scattering distribution of the radiation can be easily estimated similarly to the case in which the single scattering distribution is estimated using the single scattering simulation method. The Monte Carlo simulation is a method for obtaining an approximate solution by repeating a simulation using random numbers. Alternatively, any method may be used as long as the single scattering distribution can be estimated.

While the example in which the parameter P of the convolution kernel is determined based on the difference value Q between the scatter fractions RF has been shown in the aforementioned embodiment, the present invention is not limited to this. For example, the parameter P of the convolution kernel may be determined based on the differential value of the scatter fraction RF.

While the example in which the convolution kernel is determined using the parameter P at which the difference value Q between the scatter fractions RF is maximum (local maximum) in the graph 7 (graph 70) showing the difference values Q between the scatter fractions RF has been shown in the aforementioned embodiment, the present invention is not limited to this. The convolution kernel may be determined using the parameter P in the vicinity of the maximum (local maximum) difference value Q between the scatter fractions RF. Furthermore, the convolution kernel may be determined using the parameter P at the minimum (local minimum) value of a graph obtained by plotting the reciprocals of the difference values Q between the scatter fractions RF or in the vicinity of the minimum (local minimum) value.

Figure 10:
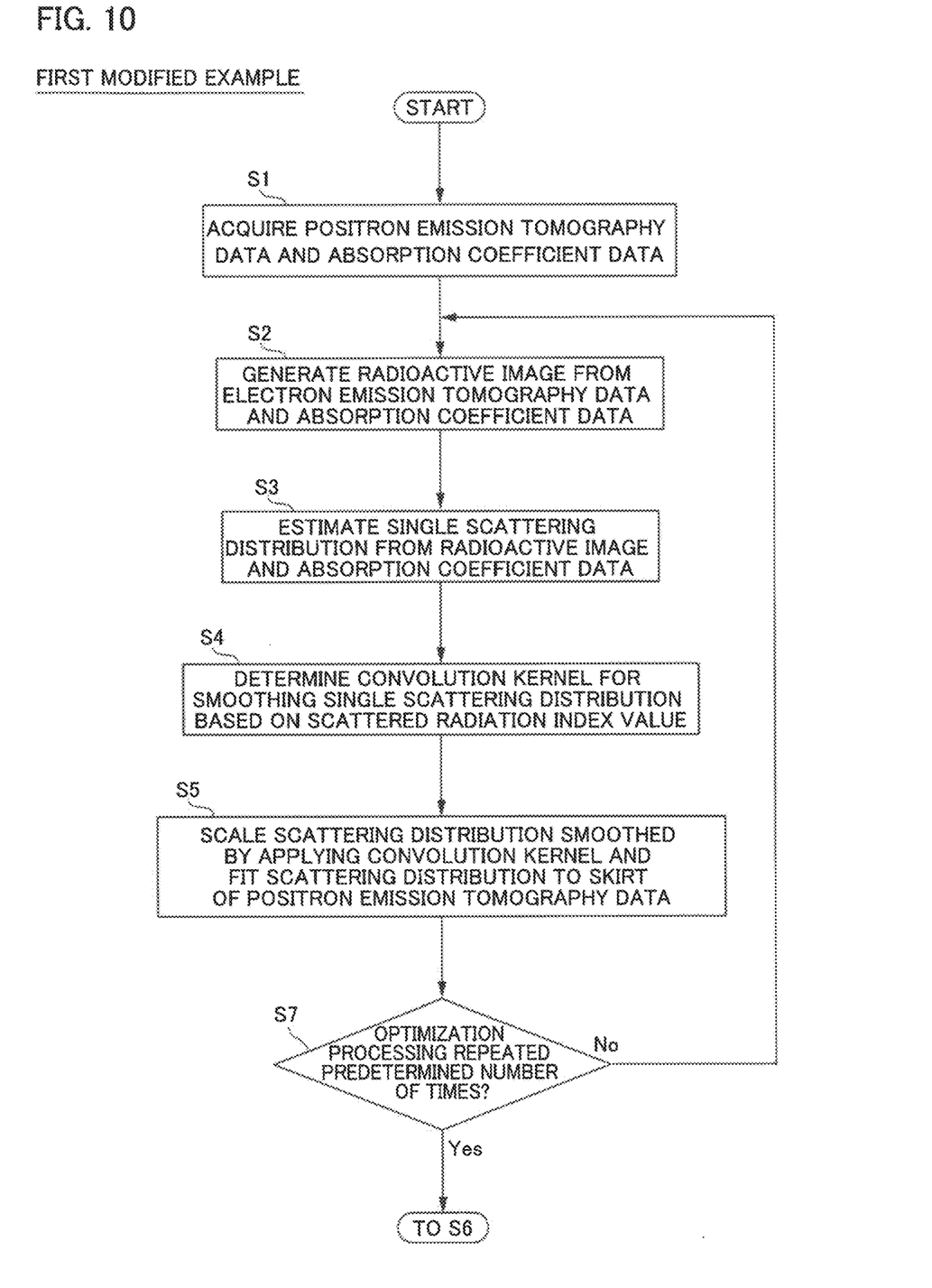
FIG. 10 is a flowchart for illustrating a scattering estimation method according to a first modified example of the embodiment of the present invention.

While the example in which the parameter P is determined by performing the processing from step S2 to step S5 has been shown in the aforementioned embodiment, the present invention is not limited to this. For example, as shown in FIG. 10, processing from step S2 to step S5 may be repeated. That is, in step S7, it is determined whether or not the convolution kernel has been optimized a predetermined number of times. When the convolution kernel has not been optimized the predetermined number of times, the processing advances to step S2. When the convolution kernel has been optimized the predetermined number of times, the processing advances to step S6. The predetermined number of times refers to the number of times in which no change is observed in the optimization of the convolution kernel, and is three or four times, for example. With such a configuration, the accuracy of the scattering correction can be improved.

Figure 11:
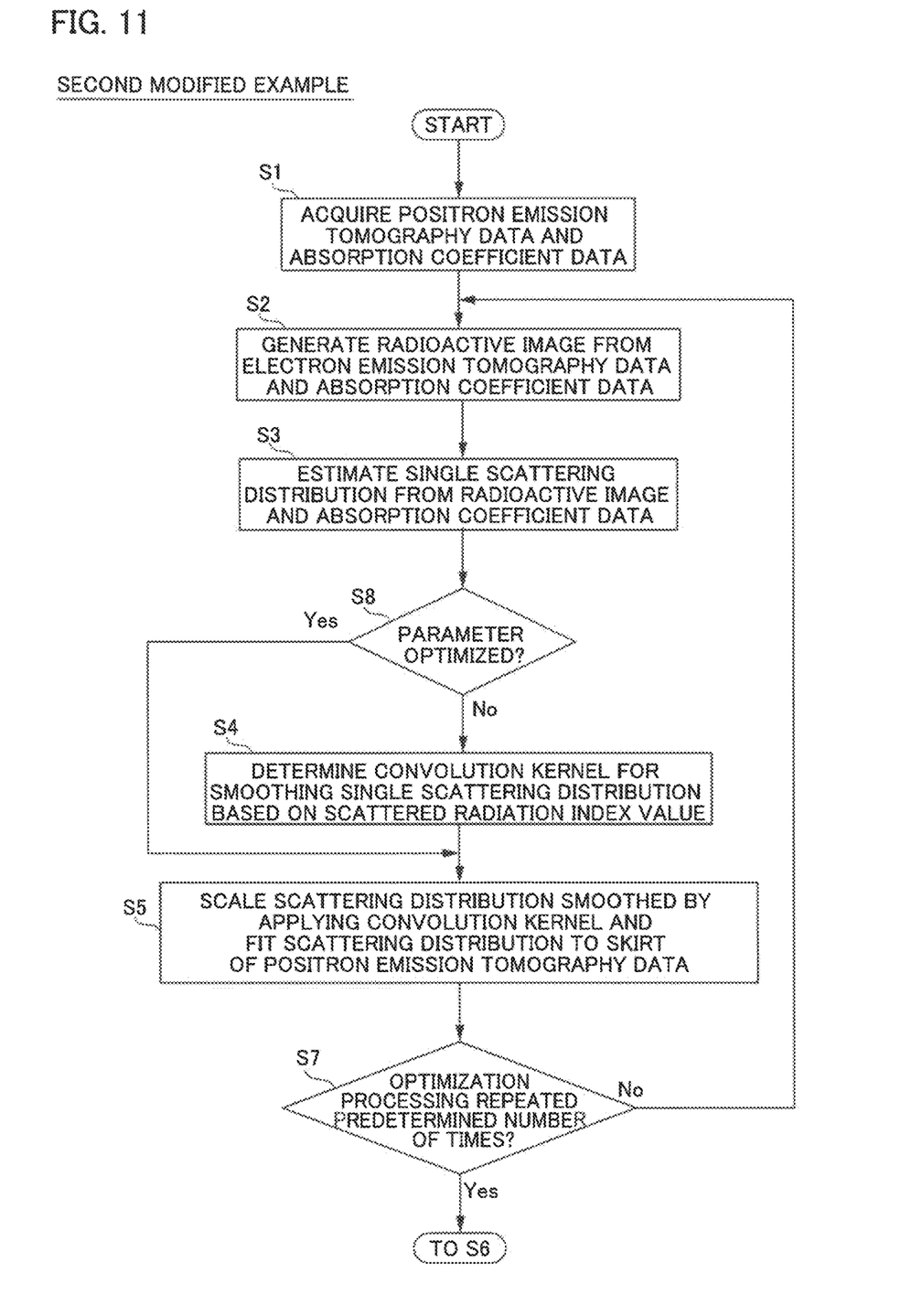
FIG. 11 is a flowchart for illustrating a scattering estimation method according to a second modified example of the embodiment of the present invention.

While the example in which the parameter P is determined by performing the processing from step S2 to step S5 has been shown in the aforementioned embodiment, the present invention is not limited to this. For example, as shown in FIG. 11, the parameter P may be determined in the first processing, and a step of determining the parameter P may be omitted in the subsequent processing after repeating. With such a configuration, the accuracy of the scattering correction can be improved while the processing time is reduced.

While the example in which the positron emission tomography measurement data and the absorption coefficient data are acquired to generate (the radioactive image 50) has been shown in the aforementioned embodiment, the present invention is not limited to this. For example, the radioactive image 5 (radioactive image 50) generated in advance and the absorption coefficient data used to generate the radioactive image 5 (radioactive image 50) may be acquired, and scattering estimation may be performed using them.

While it is assumed that data is acquired after positron emission tomography and scattering estimation is performed when the images are reconstructed in the aforementioned embodiment, the present invention is not limited to this. For example, scattering estimation may be performed in real time while imaging is performed by the positron emission tomography apparatus 1.

While the example in which data obtained by converting the form data of the subject O is acquired as the absorption coefficient data has been shown in the aforementioned embodiment, the present invention is not limited to this. For example, the image data acquirer 21 may be configured to acquire the form data of the subject O, and the form data of the subject O may be converted into the absorption coefficient data in the controller 20.

While the example in which the graph 6 (graph 60) plotting the scatter fractions RF and the graph 7 (graph 70) plotting the difference values Q between the scatter fractions RF are created has been shown in the aforementioned embodiment, the present invention is not limited to this. The parameter P at which the difference value Q between the scatter fractions RF becomes maximum (local maximum) may be determined without creating the graph 6 (graph 60) and the graph 7 (graph 70).

While the range of the parameter P is set to 5.0 bins to 20 bins, and the parameter P is varied in each of the aforementioned first and second examples, the present invention is not limited to this. The range may be set in accordance with the size of the subject O.

While the standard deviation ($\sigma$) of the Gaussian function is used as the parameter P of the convolution kernel in the aforementioned embodiment, the present invention is not limited to this. For example, the full width at half maximum (FWHM) of the Gaussian function may be used. Alternatively, as the parameter P, the half width at half maximum (HWHM) of the Gaussian function may be used. Alternatively, as the parameter P, the full width at tenth maximum (FWTM) of the Gaussian function may be used.

DESCRIPTION OF REFERENCE NUMERALS

1: positron emission tomography apparatus
2: image processor
3: display
5, 50: radioactive image
6, 60: graph of scatter fraction
7, 70: graph of difference value between scatter fractions
20: controller
21: image data acquirer
22: storage
P: parameter
Q: difference value between scatter fractions
SF: scattered radiation index value
RF: scatter fraction

The invention claimed is:

1. A scattering estimation method comprising:
acquiring positron emission tomography measurement data and absorption coefficient data;
generating a radioactive image from the positron emission tomography measurement data and the absorption coefficient data;
estimating a single scattering distribution of radiation in the radioactive image from the radioactive image and the absorption coefficient data;
determining a convolution kernel for smoothing the single scattering distribution based on a scattered radiation index value of the radioactive image; and
fitting, to the positron emission tomography measurement data, a scattering distribution smoothed by applying the convolution kernel to the single scattering distribution.

2. The scattering estimation method according to claim 1, wherein
the scattered radiation index value is a scatter fraction; and
the determining of the convolution kernel includes determining the convolution kernel based on a result of comparison between scatter fractions of radioactive images smoothed using a plurality of parameters that characterize the convolution kernel.

3. The scattering estimation method according to claim 2, wherein the determining of the convolution kernel includes determining the convolution kernel based on magnitudes of changes of the scatter fractions with changes of the plurality of parameters.

4. The scattering estimation method according to claim 2, wherein
the convolution kernel defines a weight distribution specified by a parameter relating to dispersion; and
the smoothing of the single scattering distribution is performed by a weighted average filter using the convolution kernel.

5. The scattering estimation method according to claim 1, wherein the estimating of the single scattering distribution from the radioactive image and the absorption coefficient data includes estimating the single scattering distribution by a single scattering simulation method.

6. The scattering estimation method according to claim 1, wherein the estimating of the single scattering distribution from the radioactive image and the absorption coefficient data includes estimating the single scattering distribution by a Monte Carlo simulation method.

7. An image Processor comprising:
a controller; and
an image data acquirer configured to acquire positron emission tomography measurement data and absorption coefficient data; wherein
the controller is configured to:
generate a radioactive image from the positron emission tomography measurement data and the absorption coefficient data;
estimate a single scattering distribution from the radioactive image and the absorption coefficient data;
determine a convolution kernel for smoothing the single scattering distribution based on a scattered radiation index value of the radioactive image; and
fit, to the positron emission tomography measurement data, a scattering distribution smoothed by applying the convolution kernel to the single scattering distribution.

* * * * *